United States Patent [19]
Patrick

[11] Patent Number: 5,496,827
[45] Date of Patent: Mar. 5, 1996

[54] COMPOSITIONS FOR THE TRANSDERMAL DELIVERY OF NUTRIENTS

[76] Inventor: Jay Patrick, 14 Morgan, Irvine, Calif. 92718

[21] Appl. No.: 275,437

[22] Filed: Jul. 15, 1994

[51] Int. Cl.⁶ .................................................. A61K 31/47
[52] U.S. Cl. .......................... 514/310; 514/159; 514/256; 424/70.1; 424/61; 424/400; 424/59; 424/450; 424/489
[58] Field of Search .................... 424/59, 61, 78, 424/480, 489, 70, 400; 514/159, 254, 310

[56] References Cited

U.S. PATENT DOCUMENTS

| | | | |
|---|---|---|---|
| 4,968,685 | 11/1990 | Grollier | 514/256 |
| 5,133,958 | 7/1992 | Stuckler | 424/61 |
| 5,215,759 | 6/1993 | Mausner | 424/489 |
| 5,318,960 | 6/1994 | Toppo | 514/159 |

Primary Examiner—José G. Dees
Assistant Examiner—Deboreh D. Carr
Attorney, Agent, or Firm—Charles H. Thomas

[57] ABSTRACT

A composition having therapeutic and cosmetic effects is comprised of an effective concentration of methyl nicotinate in a diluent. When such a composition is topically applied the methyl nicotinate acts to increase circulation in the area of application and also acts as a pain reliever and a muscle relaxant. The composition may also contain various vitamins, minerals and other nutrients. The methyl nicotinate also acts as a facilitator to promote the transdermal penetration of the vitamins, minerals and other nutrients into the skin.

17 Claims, No Drawings

COMPOSITIONS FOR THE TRANSDERMAL DELIVERY OF NUTRIENTS

BACKGROUND OF THE INVENTION

1. Field of the Invention

The present invention relates to a composition containing methyl nicotinate for application to a person's skin.

2. Description of the Prior Art

Vitamin B3 is considered by most to be the major B vitamin required for a healthy existence. Indeed, the U.S. Food and Drug Administration has assigned Vitamin B3 its highest MAC rating of 20 milligrams per day for an adult. This contrasts with Vitamin B1 (thiamin Hcl.) which the FDA has assigned a rating of 1.5 mg. daily and Vitamin B2 (riboflavin) at 1.7 mg. daily.

Most vitamin formulas supply Vitamin B3 as niacinamide. However, niacinamide does not have the circulatory benefits of niacin, (nicotinic acid) although niacin is converted into niacinamide in the brain to aid its function.

Niacin is found in minute quantities in all living cells. The amide form niacinamide also occurs in plants and animals, generally in enzyme systems. Poor eyesight, bad hearing, senility, loss of memory, dullness of mind, depression, arthritis and, indeed, most heart disease are related to the state of blood circulation in the human body. Niacin dilates the blood vessels and, as researchers have recently discovered, stops the clumping up of red blood cells. Red blood cells acquire a positive charge, which causes them to cling together. This clumping action which impairs circulation occurs because the red blood cell is approximately one microgram in diameter and the small capillaries of the body are of the same diameter. Thus, the blood cell often has to squeeze sideways into the capillary. Therefore, if many red blood cells clump together, these vital carriers of nutrients to some 70 trillion body cells cannot get into the capillaries. Serious damage to the body results as a consequence.

Histamine is an autacoid, a class of hormones which act on tissues of cells in the immediate area of their site of formation. Histamine is stored chiefly in the granule of the tissue mast cells and the blood mast cells. Histamine is alkaline in pH and holds a positive charge. Histamine is opposed in the granule of the mast cells by the acidic mucopolysaccharide, heparin, which has a negative charge.

The introduction of niacin into the blood stream has a significant effect on histamine. Specifically niacin releases histamine from the mast cells. As niacin "pops out" histamine, heparin is also released. Heparin then gives a negative charge to the red blood cells, which reduces the clumping and greatly improves blood circulation. Thus, the red blood cells are able to go freely, in single file, into the tiny capillaries of every part of the body, especially the brain, thereby bringing the necessary nutrients to those areas.

Niacin can be administered orally, whereupon it is converted to niacinamide in the brain. However, there is no circulatory benefit to the amide form of the vitamin. The oral ingestion of niacin in a substantial quantity, say, 30 milligrams or more, however, can result in a rather total body reaction described as "the niacin flush". In this reaction, the body becomes quite warm, especially in the area of the head, and the skin of the whole body becomes quite red. There is attendant itching, if the dosage is large enough. This flush spurs the brain and body to greater activity. However, it can be a very uncomfortable reaction for an hour or so. Timed-release, orally ingested forms of niacin have long been utilized to give the benefits of a milder niacin flush over a prolonged period of time. While many people do use timed-release, orally ingested forms of niacin, others avoid them entirely, fearing the powerful niacin flush.

Another form of Vitamin B-3 is inositol niacinate. This complex is not water soluble but oil soluble. Accordingly, when it is orally ingested, it gives, in moderate doses, only a slow, niacin warmth that can be readily tolerated by most people. Both niacin and inositol niacinate (myo-inositol hexa-3-pyridine-carboxylate) have the power to break up clots of blood like those that occur in phlebitis and to restore circulation. Adequate quantities will also prevent varicose veins and arthritis, Also, clinical studies have shown that good health has been restored to some 85% of schizophrenic patients, with high doses of niacin and Vitamin C, as reported in medical journals.

SUMMARY OF THE INVENTION

According to the invention I have discovered that an obscure form of Vitamin B-3, namely methyl nicotinate, which is rarely produced, has the power to penetrate the skin topically and limit "the niacin flush" to a specific area. This avoids the problem of the general body niacin flush. Indeed, it permits a higher concentration of niacin to be administered to a localized area than is really feasible when the whole body is involved, as with the oral or intravenous intake of niacin. Also, localized, topical applications can be made with much greater frequency than is otherwise feasible with oral or intravenous dosages.

I have also discovered that a small amount of methyl nicotinate, if applied topically in a liquid carrier, will also induce the rapid transdermal intake of other B vitamins and trace elements which are in solution with it into any given area of the body in a matter of seconds. This can be of major benefit to a person with a muscle in spasm, for instance. Within as short a time as 15 seconds, such a solution can penetrate the skin, release the histamine and heparin within the granules of the cells, relax the muscles, and largely halt the pain. Also, the topical application of such a solution almost immediately commences the healing of a wound or skin abrasion such as in acne.

To illustrate, a formula containing methyl nicotinate, other B vitamins, and three trace elements in a water diluent was administered to twenty-five people of both sexes and various ages who had severe muscle pains in the thighs. Twenty-one of the people reported immediate benefits. The remaining five found that their pains subsided within about five minutes after the preparation was applied.

Conventional analgesics almost uniformly contain up to 50% methyl salicylate, which acts in two ways: first, as a counter-irritant, and, secondly, due to its strong relationship to another salicylate, aspirin, as a pain reliever. However, methyl salicylate has such a strong odor that products for day-time use incorporate a lower level of the substance to reduce the offensive impact on others. In addition, methyl salicylate is listed in the Merck Index as a poisonous drug, so some health risk attends its use.

On the other hand, the composition which I employ utilizing methyl nicotinate contains no methyl salicylate whatsoever. Nevertheless, it functions almost instantly to relieve pain and muscle contractions, steps up the circulation, and, and the same time, introduces into the body essential B vitamins and major trace elements such as chromium, selenium, and wound-healing zinc. Thus, the product is far superior to any analgesic ever offered.

Also, the preparation was applied to the faces of twelve people suffering from various skin diseases. Within several days, all reported that their skin had improved remarkably. This is largely because the formula employed included a variety of major nutrients, including the trace element zinc, which greatly aids the body in reconstruction. The presence of methyl nicotinate in the application liquid enhanced the extent to which zinc and the other elements passed through the skin.

The ability of methyl nicotinate to carry into the body substantial quantities of other nutrients is quite evident when a considerable amount of riboflavin is present in a formula that is applied to the skin. The ratio of the riboflavin may be three parts to one of the methyl nicotinate. When applied to some area of the body rather distant from the kidneys, for instance, the shoulder, I have found the action is quite evident, as the urine emerges from the bladder with a strong yellow color reflecting the presence of the powerful yellow color of riboflavin.

For hundreds of years humans have been plagued with a complex of disease symptoms or syndrome that often seemed to have one clearly identifiable characteristic, namely rough skin. This was known in the regions of Lombardy, Italy as pelie agra, Italian for rough skin, which became anglicized to the word pellagra. The discovery of the cause of this many faceted disease proved to be one of the major achievements of biochemistry and medicine. Pellagra, it was learned, combines the symptoms of six or more different diseases. It is found among the rich as well as the poor, both urban and rural dwellers, alcoholics, teetotalers, and those on deficient diets. As a well defined disease it may be identified by the four d's: dermatitis, diarrhea, dementia, and death.

In modern times dermatitis continues to plague young people as acne and eczema. Teenagers feel stigmatized by these conditions, and can acquire life-long mental problems as a result. However, niacin and other nutrients, especially the trace element, zinc, work together to correct this ailment. Thus, recovery is quite dramatic when a solution of methyl nicotinate, which incorporates a zinc salt such as zinc aspartate, is applied to an adolescent's skin.

I have also discovered benefits of topical applications of a liquid substance containing niacin for older individuals. Indeed, I have found that, when such a substance is applied to a person's scalp over a period of many weeks or months, there is a marked improvement in growth of the hair. Indeed, some hair follicles ultimately improved so substantially as to again produce hair having the original pigmentation which one may not have had for many years in the scalp hair or beard.

I also found that with the continued application of this substance to my own face and scalp that fully pigmented hair grows out in places where it had not before appeared, high on the cheek and to the right and left of the eyebrows, in my case.

Since I discovered that methyl nicotinate has such remarkable ability to penetrate the skin, it occurred to me that, because the skin and the beard are of the same protein, namely keratin, a suitable solution containing methyl nicotinate might also aid in introducing water into the beard, which is necessary to soften the beard as an aid to shaving. I applied the same preparation containing methyl nicotinate, plus other B vitamins and trace elements, to the skin of my lower face. I observed that this application aided enormously in the shaving process. Indeed, my beard was softened so much that the life of my razor blades greatly increased. For instance, a high grade stainless steel blade (Gillette's Finest), with daily use of the preparation, lasted as long as 43 shaves giving good results every time. Also, shaving time is substantially reduced.

After the application of this solution to my shaving for many months, I noted that my eyebrows, which had been largely gray to white initially had turned dark brown, and that my sideburns were also turning brown. This change occurred at a distance of about one inch from the bottom of the sideburn, an area which was being benefitted from the application of the substance I was using as a shaving lotion. I then decided to grow a beard to see what benefit had occurred to the remainder of my hair. I discovered that my whiskers which had previously been primarily gray to white were to a large extent emerging dark brown in color as a result of local application of the solution. However, the color of whiskers in the area of the my chin did not change at all, and my mustache above my lips only partly changed. Nevertheless, the rate of growth of the hair increased to a very pronounced extent, and the continuing rapid growth has proven to be much greater than normal in a man of my age, which is eighty-two years.

I also found it remarkable that the color of my hair in the area in the lower back of my neck had also changed from gray/white to dark brown. This is probably because I had also frequently applied the preparation to the back of my neck to relieve tension and aid circulation.

It is apparent that the preparation of the present invention, when applied to the scalp and certain other areas of the body, both stimulates the circulation of the blood and provides vitamins and trace elements which promote hair growth and, in many cases, also induces restoration of the natural pigmentation of the hair.

Various compositions currently exist which have cosmetic effects when applied to the skin. Such compositions often include various vitamins or other nutrients which are applied topically and sometimes act to improve the appearance of the skin. Certain other compositions contain vitamins that are said to be absorbed through the skin and have local or systemic effects. For example, U.S. Pat. No. 3,944,550 issued to Hasunuma discloses that Vitamin E can be applied to the skin for curing chilblains, exudative erythema, frostbite, and feelings of cold. U.S. Pat. No. 4,619,829 issued to Motschan discloses that vitamins such as Vitamin A, the B vitamins, and Vitamins C, D, and E can be administered topically. Vitamins A and E are exceptions. Both A and E are extensively used as components of lotions, and E has been employed to reduce the ill effects of sunburn. However, it has heretofore been widely accepted that the B vitamins and Vitamin C have really very little power to fully penetrate the skin, and get into the capillaries and the cells.

The present invention provides a system for relieving muscular pain and a method for transdermal delivery of vitamins, minerals and other nutrients. The present invention is directed to compositions containing methyl nicotinate for dermal application. The compositions are useful as muscle relaxants, muscular pain relievers, and to stimulate capillary blood circulation in the human body. When various vitamins, minerals and other nutrients are added to the compositions, methyl nicotinate acts as a carrier and provides a means for promoting their transdermal delivery. The addition of relatively large amounts of riboflavin and cyanocobalamin to the compositions of the present invention acts further to stimulate hair growth and to aid in the return of natural pigmentation to the hair.

The compositions of the present invention are also useful in removing senile lentigines (brown spots). The compositions can be used as well to relieve the pain associated with carpal tunnel syndrome, that is arthritic pain in the joints of the fingers and toes. In addition, the compositions of the invention enhance fingernail growth.

Furthermore, the compositions of the invention ease the process of shaving by wetting out the beard. They also promote rapid healing of the skin, especially on the face, as with acne or eczema.

In one broad aspect the invention may be considered to be a skin treatment composition comprising between about 0.025 percent and about 1 percent methyl nicotinate by weight in a liquid. Preferably the composition is comprised of no more than about 0.25 percent methyl nicotinate. The preferred amount of methyl nicotinate in the composition is about 0.05 percent.

For applications in healing the skin, including use in the treatment of acne and eczema the composition preferably includes between about 2 percent and about 15 percent aloe vera by weight. In the preferred formulation the composition is comprised of aloe vera to the extent of about 4 percent. In other applications the composition is preferably comprised of between about 0.01 percent and about 1 percent by weight of vitamins and minerals selected from the group consisting of thiamin, riboflavin, pyridoxine, panthenol, folic acid, cyanocobalamin, para aminobenzoic acid, zinc, magnesium, manganese, chromium, selenium, and biotin. The active components are preferably applied in a liquid carrier of distilled water or a mixture of ten to twenty-five percent alcohol in water.

I have discovered that effective treatment of muscular pain and stiffness can be achieved with compositions for dermal application which include an effective concentration of methyl nicotinate. This concentration should be between about 0.25 percent and about 1.0 percent by weight in a liquid carrier. The concentration is preferably no greater than about 0.25 percent.

Methyl nicotinate is a highly active form of the B Vitamin nicotinic acid or niacin (3-pyridinecarboxylic acid). Nicotinic acid is known to have marked pharmacological activity in humans, including the nitroid reaction which is similar to the effects of histamine. Shortly after systemic administration of nicotinic acid, there is a marked flushing of the face, neck and arms due to transient vasodilatation. The vasodilatation results in increased peripheral blood flow and a rise in cutaneous temperature.

However, methyl nicotinate in a diluent is absorbed through the skin following dermal application, causing vasodilatation and an accompanying flush only in the area of application. I have found that methyl nicotinate aids in the healing of ailments, such as dermatitis by increasing circulation in the area of application, and, also, by facilitating the acceptance through the skin of other B vitamins, aloe vera, and trace elements.

In addition to vasodilatation and stimulation of circulation, dermal application of methyl nicotinate has also been found to induce relaxation of the muscles beneath the skin in the area of application. This results in the reduction of the muscular pain caused by conditions such as excessive contraction, or muscle damage produced by tears or sprains. The composition of the invention has therefore been found to act as a local analgesic, reducing the pain associated with these conditions.

It is one of the surprising discoveries of the present invention that methyl nicotinate when combined with various vitamins, minerals and other nutrients, acts as a facilitator for the transdermal delivery of these active substances through the skin, where they are rapidly absorbed into the bloodstream. Such transdermally delivered vitamins include riboflavin, cyanocobalamin, and the natural emollient, aloe vera. Also transdermally delivered are the trace elements selenium, manganese, chromium and zinc. When the vitamin riboflavin is incorporated into a diluent containing methyl nicotinate and applied to the skin covering the shoulder, I found that the urine later produced is bright yellow, indicating that the riboflavin had been transdermally delivered into the bloodstream.

One advantage of transdermal delivery of vitamins, minerals and other nutrients and emollients over oral or intravenous delivery is that the nutrients get into the blood stream in their pristine state, unaffected by the hydrochloric acid of the stomach and the digestive tract. Furthermore, they enter the blood stream and the body cells almost immediately, without the long delay involved in digestive absorption. Thus, the preparation could be useful in aiding people suffering from various types of trauma.

In an emergency, application of the product to a wide area of skin could result in large amounts of vital nutrients being passed into circulation in the body almost immediately. Thus, the product could be included in first aid kits, as it can be used by medically unskilled persons who cannot administer hypodermic injections. It can be safely applied to a stricken person's body while awaiting the arrival of the ambulance. It also can be furnished as a vitamin and nutrient supplement in a delivery system that will help to assure people of receiving B vitamins and several important trace elements into their body organs. Due to genetic variations, some nutrients that are orally ingested follow the wrong pathways in the bodies of some people. This is an obvious factor in allergies. Transdermal entry of vitamins and other nutrients should avoid this problem in many cases.

I have further discovered that a composition comprising methyl nicotinate, all of the B vitamins, with relatively high levels of riboflavin and cyanocobalamin, plus the trace elements chromium, selenium, and zinc acts to stimulate hair follicles. This results in increased hair growth and the restoration of pigmentation of the hair. When applied to the skin of the face and scalp for a period of approximately three or four months, loss of hair was reduced and a substantial amount of hair growth returned to areas of the head from which hair had ceased to grow. In addition, the composition caused the natural pigmentation of the hair to return in some, but not all, areas.

The compositions of the present invention can be made by dissolving methyl nicotinate and various other vitamins and trace elements in a diluent such an distilled water to form an aqueous solution. An alcohol, such as ethanol at a concentration of 10% to 25% is preferably added to the solution. Propylene glycol may be added for its coupling power and glycerin, aloe vera, lanolin, and other substances may be added as emollients.

EXAMPLE 1

A preferred formulation of the present invention comprises the following active components in the following amounts per composition volume of two fluid ounces:

| | |
|---|---|
| Thiamin Hal | 4.5 milligrams |
| Riboflavin | 10.0 milligrams |
| Methyl Nicotinate | 30.0 milligrams |
| Pyridoxine Hal | 60.0 milligrams |
| dl Panthenol | 150.0 milligrams |

|                              |                   |
| ---------------------------- | ----------------- |
| Folic Acid                   | 6.0 milligrams    |
| Cyanocobalamin               | 15.0 milligrams   |
| PABA                         | 46.0 milligrams   |
| Zinc (gluconate)             | 1.65 milligrams   |
| Magnesium (citrate)          | 1.0 milligrams    |
| Manganese (gluconate)        | 1.0 milligrams    |
| Chromium (picolinate)        | 3.0 micrograms    |
| Selenium (selenomethionine)  | 600.0 micrograms  |
| Aloe vera                    | 3.0 grams         |
| d-Biotin                     | 5.0 micrograms    |

In the preferred formulation, the active components in the amounts listed above are mixed with distilled water to a total volume of approximately two fluid ounces. The amounts of the active components can be adjusted proportionately depending on the total amount of solution which is to be prepared.

The concentration of the active components can be varied widely, but preferably remains within 20-fold of the concentrations specified in the preferred formulation. However, an increase of the methyl nicotinate level by more than 5-fold tends to produce a rather pronounced pruritus (itching of the skin).

An 82-year-old white male subject initially having gray hair, gray sideburns and gray eyebrows used the composition described in the preferred formulation daily on his scalp and also on his lower face for two months prior to shaving. He then noticed dark hair growing out of his eyebrows, and, in addition, it also became obvious that hair was emerging in a dark brown color about one inch up from the bottom of his sideburns. The subject then started growing a beard. Prior to treatment, the subject's facial hair was gray to white. Yet the hair that then grew in was dark brown on his cheeks and on the back of his neck. However, the hair on his chin and the front of his throat remained white.

The subject's hair loss drastically declined within approximately six weeks of commencement of the scalp application. After using the composition, the subject noticed only three or four hairs at most on his comb or brush in the morning, whereas, before using the composition, he noticed much more hair on his comb or brush.

EXAMPLE 2

The formulation of Example 1 is repeated but with a substitution of a mixture of 25 percent ethanol in distilled water for the diluent or carrier employed in Example 1. The resulting composition can be utilized in the same manner described above.

EXAMPLE 3

The composition is formulated as in Example 1 but with the addition of 20 milligrams methyl cellulose as a thickening agent to the active ingredients listed in Example 1. The use of a small amount of methyl cellulose in the formulation is preferable when the composition is to be employed as a skin lotion.

To establish the penetration of the product into the skin, the following testing procedure was followed. A quantity of 1.1 grams of the preparation was worked into both sides of the subject's hands. For 15 minutes thereafter the subject avoided touching anything. He then immersed his hands, alternately, into 150 milliliters of distilled water in a beaker, working each hand around in the water for one minute. After immersion each hand was then slowly withdrawn, allowing the water to drip back into the beaker before the hand was dried. The above procedure was followed five times, with immersion of the hands in the same water. The rinse water was then sent to an independent testing laboratory for determination of its vitamin and mineral content. Analysis of the water showed that methyl cellulose was present but the rinse water contained no detectable vitamins or minerals. Thus, it is apparent that the vitamins and minerals were absorbed through the skin.

The composition of this example was used on both the backs and the fronts of the hands of the same 82-year old subject described in Example 1. Initially the subject had senile lentigines (brown spots) on the backs of his hands. For two months about 1.1 grams of the product were worked into both sides of the subjects hands for about one minute on a daily basis. The composition dried almost instantly and left no sticky feeling when applied. The subject avoided washing his hands for at least fifteen minutes after each application. After six months most of the lentigines had faded so as to be only faintly observable. The preparation appears to enter the cells and exert a rinsing action that pulls out the brown matter within the cell. However, this takes many months of application of the preparation to the affected area.

As a skin lotion, the product leaves light deposits of aloe vera and lanolin within the outer layers of the skin. Some people quickly get annoying "hang nails" after prolonged immersion of the hands in hot water containing a powerful detergent, as in dish washing. Yet, if the preparation is applied immediately to the skin after washing dishes, no "hang nails" ever appear. Indeed, the product serves as a truly remarkable hand lotion, which dries within less than a minute and leaves the hands soft and pink in color as a result of release of the histamine.

The formulation of the present example, if applied to the fingers of users, also enhances fingernail growth. This formulation was tested for a period of three months on ten women. That is, each of the women utilized a quantity of the product, working it into their hands for about one minute on a daily basis for a three-month period. The subjects avoided washing their hands for at least fifteen minutes following each application. At the end of three months fingernail growth had increased an average of 52 percent above the normal average of 0.104 to 0.108 millimeters per day. Also, the appearance and strength of the nails was improved as reported by fifteen different women who utilized the product in a similar manner. It is believed that this is due, in part, to the presence of zinc in the formulation, and also to increased circulation in the hands that are used to apply the preparation to other parts of the body.

The compositions of the present invention can also be used to ease the process of shaving by wetting out the beard. Best results are obtained when the compositions are applied to the areas of skin to be shaved, followed by warm water on a wash cloth, then shaving cream.

It is to be understood that in addition to the named components recited in the examples above, the composition of the present invention can contain other vitamins and minerals. Also it can employ other ingredients such as fragrances, colorants, preservatives and emulsifiers without departing from the scope of the invention. Furthermore, while certain preferred embodiments have been described, it will be apparent to those of skill in the art that various other modifications may be made to these formulations without departing from the scope of the invention. Accordingly, the scope of the invention should not be construed as limited to the specific examples described.

I claim:

1. A transdermal nutrient delivery composition comprising, in a liquid, between about 0.025 percent and about one percent methyl nicotinate by weight and between about 0.01 percent and about one percent by weight of vitamins and minerals selected from the group consisting of thiamin, riboflavin, pyridoxine, panthenol, folic acid, cyanocobalamin, para aminobenzoic acid, zinc, magnesium, manganese, chromium, selenium, and biotin.

2. A composition according to claim 1 comprising no more than about 0.25 percent methyl nicotinate.

3. A composition according to claim 2 comprising about 0.05 percent methyl nicotinate.

4. A composition according to claim 2 further comprising between about 2 percent and about 15 percent aloe vera by weight in said liquid.

5. A composition according to claim 4 further comprising about 4 percent aloe vera.

6. A composition according to claim 1 wherein said liquid is comprised of water.

7. A composition according to claim 6 wherein said liquid is further comprised of alcohol.

8. A skin application substance comprising between about 0.025 percent and about one percent methyl nicotinate and at least about 0.01 percent vitamins and minerals selected from the group consisting of thiamin, riboflavin, pyridoxine, panthenol, folic acid, cyanocobalamin, para aminobenzoic acid, zinc, magnesium, manganese, chromium, selenium, and biotin by weight in a liquid.

9. A skin application substance according to claim 8 comprising no more than about 0.25 percent nicotinate.

10. A skin application substance according to claim 9 comprising about 0.05 percent methyl nicotinate.

11. A skin application substance according to claim 10 further comprising by weight between about 0.02 percent and 0.05 percent vitamins and minerals selected from the group consisting of riboflavin, cyanocobalamin, and selenium.

12. A skin application substance according to claim 9 further comprising between about 0.001 percent and about 0.005 percent zinc.

13. A skin application substance according to claim 9 wherein said liquid is comprised of water.

14. A skin application substance according to claim 13 wherein said liquid is further comprised of alcohol.

15. A medicating composition for dermal application comprising methyl nicotinate present to the extent of between about 0.025 percent and about one percent and at least about 0.01 percent vitamins and minerals selected from the group consisting of thiamin, riboflavin, pyridoxine, panthenol, folic acid, cyanocobalamin, para aminobenzoic acid, zinc, magnesium, manganese, chromium, selenium, and biotin by weight in a liquid substance.

16. A medicating composition according to claim 15 further comprising between about 0.01 percent and about one percent vitamins and minerals selected from the group consisting of thiamin, riboflavin, pyridoxine, panthenol, folic acid, cyanocobalamin, para aminobenzoic acid, zinc, magnesium, manganese, chromium, selenium, and biotin.

17. A medicating composition according to claim 15 wherein said liquid substance is a diluent comprised of water.

* * * * *